(12) United States Patent
Essenreiter et al.

(10) Patent No.: US 7,251,522 B2
(45) Date of Patent: Jul. 31, 2007

(54) X-RAY IMAGE-ASSISTED NAVIGATION USING ORIGINAL, TWO-DIMENSIONAL X-RAY IMAGES

(75) Inventors: Robert Essenreiter, München (DE); Falko Seifferth, Zorneding (DE); Robert Schmidt, Kirchheim (DE); Mario Zeiss, Poing (DE); Sorin-Alexandru Neagu, Erlangen (DE); Matthias Mühlhäusser, Herzogenaurach (DE); Anders Steiner, Nürnbert (DE)

(73) Assignee: BrainLAB AG, Feldkirchen (DE)

( * ) Notice: Subject to any disclaimer, the term of this patent is extended or adjusted under 35 U.S.C. 154(b) by 438 days.

(21) Appl. No.: 10/661,834

(22) Filed: Sep. 12, 2003

(65) Prior Publication Data

US 2004/0082854 A1    Apr. 29, 2004

Related U.S. Application Data

(60) Provisional application No. 60/440,702, filed on Jan. 17, 2003.

(30) Foreign Application Priority Data

Sep. 12, 2002   (EP) .................................. 02020474

(51) Int. Cl.
    *A61B 5/05* (2006.01)
(52) U.S. Cl. ........................ 600/424; 600/429; 606/130
(58) Field of Classification Search ........ 600/424–429, 600/407; 606/130; 378/21, 37, 62, 63, 18, 378/20, 207
    See application file for complete search history.

(56) References Cited

U.S. PATENT DOCUMENTS

| 5,222,499 | A | | 6/1993 | Allen et al. |
| 6,149,592 | A | * | 11/2000 | Yanof et al. ................. 600/427 |
| 6,351,573 | B1 | | 2/2002 | Schneider |
| 6,484,049 | B1 | * | 11/2002 | Seeley et al. ............... 600/426 |
| 6,493,574 | B1 | * | 12/2002 | Ehnholm et al. ........... 600/429 |
| 2003/0185346 | A1 | * | 10/2003 | Vilsmeier .................... 378/165 |
| 2004/0037390 | A1 | * | 2/2004 | Mihara et al. ................. 378/65 |

FOREIGN PATENT DOCUMENTS

| DE | 198 07 884 | 9/1999 |
| DE | 199 17 867 | 11/2000 |

* cited by examiner

Primary Examiner—Brian L. Casler
Assistant Examiner—John F. Ramirez
(74) Attorney, Agent, or Firm—Renner, Otto, Boisselle and Sklar, LLP

(57) ABSTRACT

A method for displaying images in a medical navigation system assisted by x-ray images includes calibrating an x-ray device in the medical navigation system and producing a plurality of two-dimensional x-ray images of a patient using the x-ray device. During the producing step, positions of the x-ray device are determined using the medical navigation system in order to produce positional data. Data associated with the two-dimensional x-ray images is converted into three-dimensional data. The two-dimensional x-ray images, production information corresponding to the two-dimension x-ray images, and the three-dimensional data to the navigation system. At least the two-dimensional x-ray images are displayed on an image output of the medical navigation system.

11 Claims, 2 Drawing Sheets

US 7,251,522 B2

X-RAY IMAGE-ASSISTED NAVIGATION USING ORIGINAL, TWO-DIMENSIONAL X-RAY IMAGES

RELATED APPLICATION DATA

This application claims priority of U.S. Provisional Application No. 60/440,702, filed on Jan. 17, 2003, which is incorporated herein by reference in its entirety.

FIELD OF THE INVENTION

The present invention relates to x-ray image-assisted navigation in the area of medicine. It provides a method for displaying images in a medical navigation system assisted by x-ray images.

BACKGROUND OF THE INVENTION

Modern, computer-assisted surgery is able, with the aid of medical navigation systems, to show the surgeon's instruments or implants in relation to anatomical image data on a monitor during the operation. The anatomical image data of a patient can be acquired either pre-operatively or intra-operatively and can consist of various modalities (CT, MRI, PET, SPECT, x-ray images or combinations of these).

In computer-assisted surgery, it is also common to ascertain image data with the aid of an x-ray device, generally used in the form of a C-arm, and to then utilize this data with the aid of a navigation system. The computer system processes the image data and "registers" it, i.e., the system determines the exact position of image data in relation to a previously defined reference, for example, spatially on the patient. It is then possible to show the position of an instrument on top of the data obtained, i.e., to navigate.

X-ray-based navigation has the advantage that it enables the surgeon, through a very simple registering method, to easily, simply, and quickly enlist the aid of navigation. In isolation, x-ray navigation provides a valuable aid for the surgeon. However in the methods currently used, it has the disadvantage that every image has to be registered individually and then displayed in correct relation to the instruments or apparatus.

Furthermore, systems exist which use navigation based on volume data sets (for example, CT, MRI) and x-ray images and/or reconstructed x-ray images, which are to be registered individually and are reconstructed from the volume data set or from processed x-ray image sets. While these x-ray images, in their original state, actually provide very good imaging data with a high contrast and good accuracy of detail, these advantages are partly lost when the data is converted into a 3D volume data set or is calculated back again to reconstructed x-ray images. In this case, the surgeon then has to navigate using image data which image content is not as good as that of the originally acquired x-ray images.

A surgical navigation system including a reference and localizing frame is known from WO 96/11624. U.S. Pat. No. 5,980,535 discloses a device for an anatomical tracking method in which positional signals are processed, which originate from a reference object on a swing arm of a head clamp.

U.S. Pat. No. 6,314,310 B1 discloses an x-ray-guided surgical localizing system with an extended mapping volume in which x-ray images from a fluoroscope (C-arm) x-ray device are registered in relation to surgical instruments via reference elements. A method and a device for the image-assisted treatment of treatment targets, including the integration of x-ray detection and a navigation system, is known from DE 199 17 867 A1. U.S. Pat. No. 6,048,097 demonstrates an x-ray examining device comprising a C-arm, wherein isocentric irradiation is performed in at least one position of the C-arm.

SUMMARY OF THE INVENTION

It is an object of the present invention to provide a method for x-ray image-assisted navigation, which overcomes the aforementioned disadvantages of the prior art. In particular, the intention is to ensure that the surgeon is provided with x-ray images for navigation which are accurate in their detail. Furthermore, the intention is to avoid or minimize the elaborate individual registration of x-ray images produced intra-operatively.

According to one aspect of the invention, the invention is directed to a method for displaying images in a medical navigation system assisted by x-ray images. A plurality of x-ray images of a patient from different positions are produced using an x-ray device, which has been calibrated in the navigation system in advance, while the position of the x-ray device is determined using a medical navigation system. The patient data obtained from the x-ray images produced is evaluated and spatially converted by processing it in the x-ray device system based on the calibration. The original two-dimensional x-ray images and the production information corresponding to the x-ray images are transferred to the navigation system along with the evaluated and converted patient data. The two-dimensional x-ray images are displayed on an image output of the navigation system to assist navigation.

One advantage of the method in accordance with the invention is substantiated in providing the original, two-dimensional x-ray images. These x-ray images are truer to detail than the conventionally used x-ray images reconstructed from the volume data set, and they exhibit a better contrast. Furthermore, it is easier for surgeons, who are accustomed to interpreting two-dimensional x-ray images, to also interpret these original x-ray images in their usual form during navigation. Since the patient x-ray images produced are registered in the navigation system as soon as they are produced, and the image data together with the registering information are provided for all the images, it is no longer necessary to individually and separately register each of the x-ray images produced in order to enable navigation.

The surgeon can choose to navigate by the three-dimensional representations (volume data set) produced from the image data obtained or to navigate by the usual two-dimensional x-ray images, already registered in advance. Navigation can also be performed simultaneously in all the image representations. The original two-dimensional x-ray image data can be visualized. For example, it is possible for the surgeon to "leaf through" these images until he finds the desired or most informative image for navigation. It is also advantageous that navigation with the aid of the two-dimensional x-ray images is possible without additional registering.

In order to calibrate the x-ray device, its position can advantageously be ascertained in relation to a calibration phantom, which can be detected by the navigation system. In accordance with one embodiment of the invention, transformational matrices concerning the spatial position of the x-ray images recorded are produced while calibrating the x-ray device. In this way, the transformational matrices assigned to the individual x-ray images can also be transferred to the navigation system when the original two-dimensional x-ray images are transferred.

In one embodiment, a C-arm x-ray device is used as the x-ray device in the method in accordance with the invention. The C-arm x-ray device can produce x-ray images in various rotational positions, such as in a series of isocentric x-ray images.

The invention further relates to a program which, when running on a computer or loaded onto a computer, causes the computer to perform steps of one of the aforementioned methods. It also relates to a computer program storage medium, which includes a program such as has been defined above.

BRIEF DESCRIPTION OF THE DRAWINGS

The invention will now be illustrated in more detail by way of the enclosed figures and by means of an example embodiment. There is shown.

DETAILED DESCRIPTION OF THE INVENTION

Figure 1:
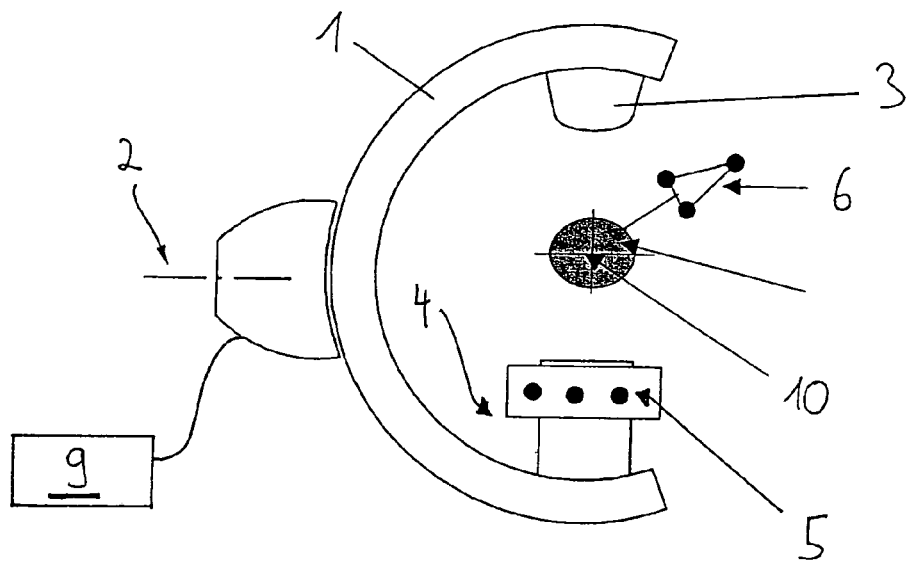
FIG. 1 is a schematic illustration of a C-arm x-ray device used in conjunction with a calibration step in accordance with the present invention.
Figure 2:
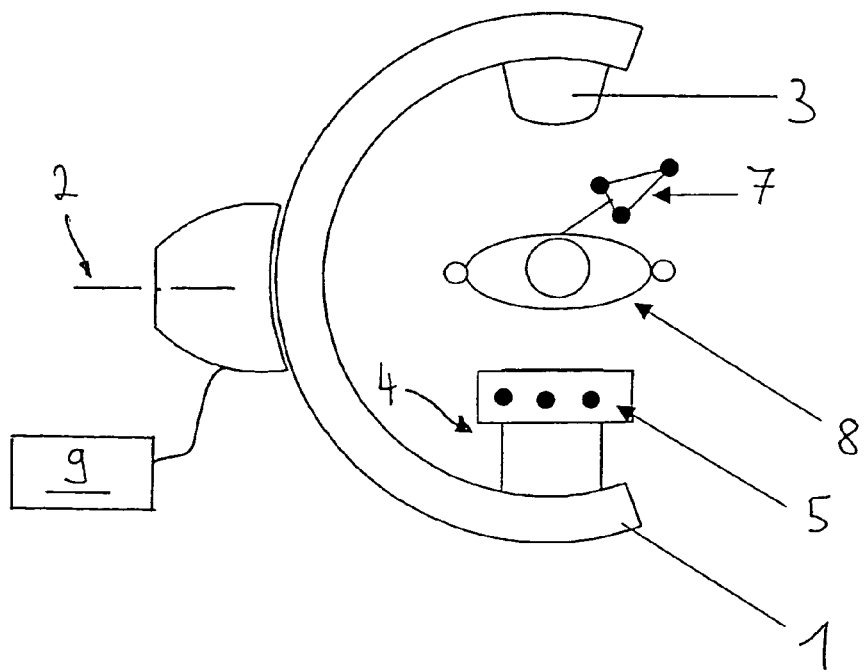
FIG. 2 is a schematic illustration of the C-arm x-ray device of FIG. 1 used in conjunction with an image recording step in accordance with the present invention.

With reference to FIG. 1, a C-arm x-ray device 1 includes an arm, which can rotate about an axis 2 for recording x-ray images, such that, for example, a series of isocentric x-ray image recordings can be produced. The C-arm x-ray device 1 includes a radiation source 3 on an upper side and an image recorder 4 on an opposite side. In one embodiment, the image recorder 4 supports a calibration attachment, which can include a first marker geometry 5. A navigation system 9, which is shown schematically, can positionally detect and track positions of the C-arm (for example, via the marker geometry 5), and positions of objects present in the x-ray device radiation field. For example, the navigation system 9 can detect and track positions of a calibration phantom 10 (via its associated marker geometry 6), as shown in FIG. 1, or a patient 8 (via its associated marker geometry 7), as shown in FIG. 2. This position detection can be accomplished, for example, using cameras. Alternatively, data detected and possibly already processed by the C-arm x-ray device 1 can be transferred to the navigation system 9 via a data connection (not shown). While the present invention is described in conjunction with a C-arm x-ray device, it is to be appreciated that the present invention finds application in conjunction with other x-ray device geometries, configurations or arrangements.

With continued reference to FIG. 1, the C-arm x-ray device 1 is shown during a calibration process, wherein the calibration phantom 10, including the associated marker geometry 6, is introduced into a beam path of the radiation source 3. The marker geometry 6 associated with the calibration phantom 10 can be identified by the navigation system 9.

FIG. 2 shows the C-arm x-ray device during the acquisition of patient 8 x-ray images, where the patient 8 lies in the beam path of the radiation source 3. During this process, the marker geometry 7 associated with the patient 8 can be detected by the navigation system 9.

With continued reference to FIGS. 1 and 2, steps of the method in which pre-calibrated data is used to enable navigation from two-dimensional and three-dimensional data simultaneously will be described in accordance with one embodiment of the invention. For purposes of simplicity of explanation, the following methodology is described as a series of steps. However, it is to be understood and appreciated that the present invention is not limited to the order of steps described below. In addition, not all described steps may be required to implement a methodology in accordance with an aspect of the invention. Furthermore, additional steps can be added to the methodology described herein without departing from the scope of the present invention.

In a first step, the C-arm x-ray device 1 used for navigation is calibrated in relation to the calibration phantom 10. The position of the C-arm x-ray device 1 in relation to the position of the phantom 10 is recorded by the camera system of the navigation system 9. As is described more fully below, this calibration enables the two-dimensional data acquired on the patient 8 to be converted, with the aid of transformational matrices, while the images are recorded; referenced with respect to each other; and used for three-dimensional navigation.

After calibration, data can be acquired on the patient 8 (FIG. 2). To this end, the position of the C-arm x-ray device 1 in relation to the patient 8 is recorded by the camera system of the navigation system 9. Once the position of the C-arm x-ray device 1 in relation to the patient 8 has been determined, a plurality of two-dimensional x-ray images can recorded. With the aid of calibration, the two-dimensional x-ray images are placed in relation to each other and to the C-arm x-ray device 1 and, therefore, to the patient 8.

Once acquisition of the two-dimensional data has been concluded, the data is converted into three-dimensional data with the aid of the transformational matrices ascertained by calibration. The three-dimensional data is transferred to the navigation system 9 and can then be readily used for computer-assisted surgery, because it is already registered in relation to the patient 8 by the earlier determination of the position of the C-arm x-ray device 1.

The two-dimensional x-ray image data, however, remains in its original form. For example, the two-dimensional x-ray image data can remain in a memory of the C-arm x-ray device 1 as it was obtained, using the corresponding transformational matrices. In one embodiment, not only the positional information (the transformational matrix) of the three-dimensional data is then transferred to the navigation system 9, but also the two-dimensional data and the respective corresponding individual transformational matrices for each two-dimensional x-ray image. The original data, which is available together with the necessary spatial positional information anyway, can therefore be utilized for navigation on the strength of the original image content, and can, for example, be displayed as shown in FIG. 3.

Figure 3:
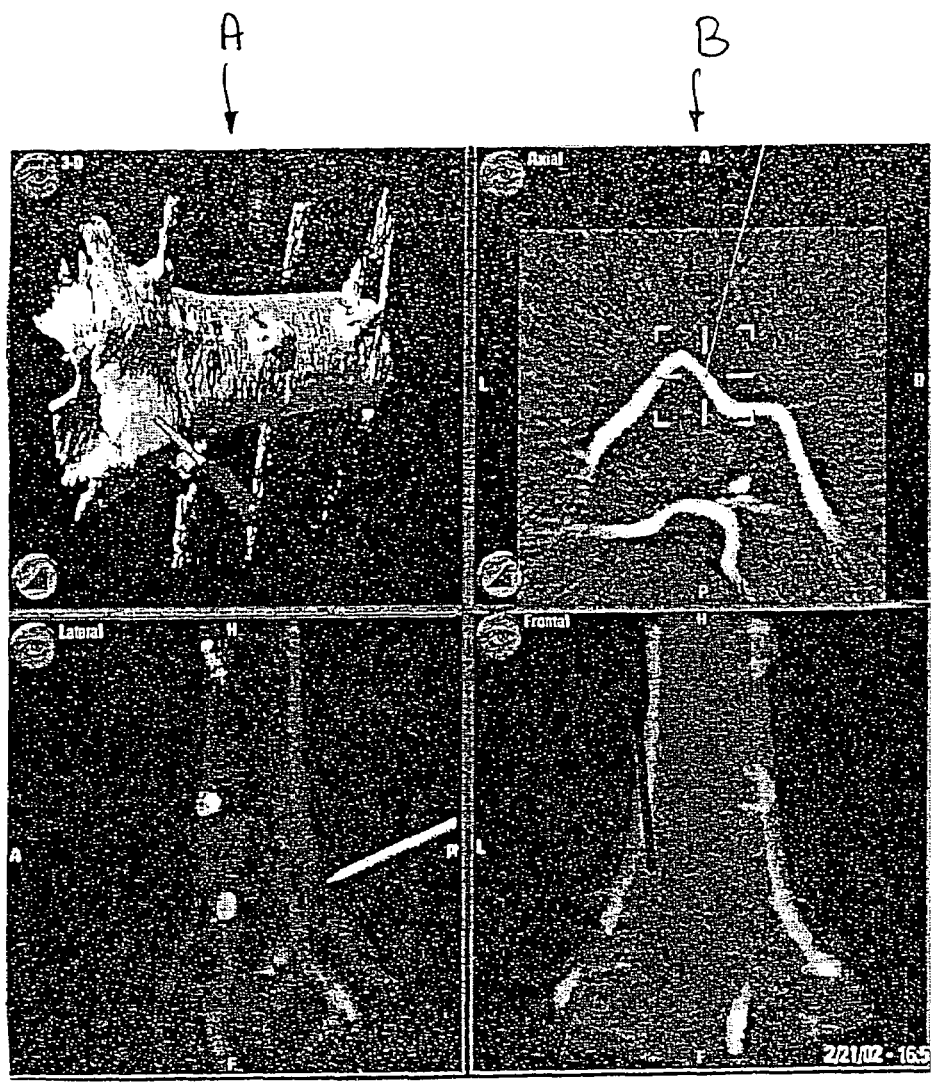
FIG. 3 is an exemplary image representation such as can be provided in accordance with the invention.

FIG. 3 shows an exemplary image output of a navigation system in accordance with one embodiment of the invention. The image output can include at least four images. These images can include the 3D representation A obtained from the three-dimensional converted volume data set and three two-dimensional representations including, for example, an axial image representation B, a lateral image representation C and a frontal image representation D. It is to be appreciated that the two-dimensional representations B, C, D are not conventional reconstructions of 2D images from the 3D data set used for representation A, but rather the original x-ray images acquired using the C-arm x-ray device 1.

As discussed above, these images B, C, D have already been registered in advance, as they were produced. The images B, C, D are available in the navigation system 9 for each individual transformational matrix at the time of being produced, because they have been separately transferred with the 2D representation. During an operation, a surgeon can work both from the original two-dimensional x-ray images B, C, D and from the three-dimensional representation A as well as a combination of these navigation options. The advantages of this include improved quality of representation of the original two-dimensional x-ray images, as compared to the calculated three-dimensional data. In addition, the original two-dimensional x-ray images include improved contrast and improved accuracy of detail. Further, it is generally easier for the surgeon to navigate from these usual x-ray images, which are accurate in their detail, because, from his training, the surgeon is typically already accustomed to interpreting such images.

The two-dimensional and three-dimensional data are advantageously registered automatically and particular types of visualization are possible. In one embodiment, a surgeon can "leaf through" or otherwise browse through a series of x-ray images B, C and D until the surgeon has found the optimum image for navigation.

In accordance with one aspect of the invention, the surgeon is provided with x-ray images for navigation which are accurate in their detail. Furthermore, the intention is to avoid or minimize the elaborate individual registration of x-ray images produced intra-operatively.

Although particular embodiments of the invention have been described in detail, it is understood that the invention is not limited correspondingly in scope, but includes all changes, modifications and equivalents.

What is claimed is:

1. A method for displaying images of a patient in a medical navigation system assisted by x-ray images, said method comprising:
   calibrating an x-ray device in the medical navigation system to obtain registering information enabling an x-ray image acquired by the x-ray device in any one of a plurality of different positions to be registered in the navigation system;
   using the calibrated x-ray device to produce a plurality of two-dimensional x-ray images of the patient from different positions;
   during the producing step, determining positions of the x-ray device using the medical navigation system, said determining step producing positional data;
   using the x-ray images, positional data and registration information to produce three dimensional image data registered in the navigation system; and
   using the registered three dimensional data and/or two dimensional x-ray images to display images on an image output device for use during a medical procedure.

2. The method as set forth in claim 1, the calibrating step includes determining a position of the x-ray device in relation to a calibration phantom using the navigation system.

3. The method as set forth in claim 1, wherein the calibrating step includes producing transformational matrices concerning spatial positions of the two-dimensional x-ray images.

4. The method as set forth in claim 3, wherein the transformational matrices assigned to individual two-dimensional x-ray images are also transferred to the navigation system when the two-dimensional x-ray images are transferred.

5. The method as set forth in claim 1, wherein the calibrating and producing steps are performed using a C-arm x-ray device.

6. The method as set forth in claim 5, wherein the step of producing a plurality of two-dimensional x-ray images includes producing a series of isocentric x-ray images.

7. A program embodied in a computer-readable medium for displaying images of a patient in a medical navigation system assisted by x-ray images, said program comprising:
   code that calibrates an x-ray device in the medical navigation system to obtain registering information enabling an x-ray image acquired by the x-ray device in anyone of a plurality of different positions to be registered in the navigation system;
   code that commands the calibrated x-ray device to produce a plurality of two-dimensional x-ray images of the patient from different positions;
   code that, during the production of the x-ray images, determines positions of the x-ray device using the medical navigation system, said determination producing positional data;
   code that uses the x-ray images, positional data and registration information to produce three dimensional image data registered in the navigation system; and
   code that uses the registered three dimensional data and/or two dimensional x-ray images to display images on an image output device for use during a medical procedure.

8. A computer program embodied on a machine-readable medium having stored thereon sequences of instructions that, cause at least an x-ray device and a navigation system to:
   calibrate the x-ray device in the medical navigation system to obtain registering information enabling an x-ray image acquired by the x-ray device in any one of a plurality of different positions to be registered in the navigation system;
   use the calibrated x-ray device to produce a plurality of two-dimensional x-ray images of the patient from different positions;
   determine positions of the x-ray device using the medical navigation system to produce positional data;
   use the x-ray images, positional data and registration information to produce three dimensional image data registered in the navigation system; and
   use the registered three dimensional data and/or two dimensional x-ray images to display images on an image output device for use during a medical procedure.

9. The method as set forth in claim 1, further comprising displaying at least the two-dimensional x-ray images on the image output of the medical navigation system.

10. The program as set forth in claim 7, further comprising code that displays at least the two-dimensional x-ray images on the image output of the medical navigation system.

11. The program as set forth in claim 8, wherein the instructions further cause at least the x-ray device and/or the navigation system to display at least the two-dimensional x-ray images on the image output of the medical navigation system.

* * * * *